United States Patent
Wang et al.

(10) Patent No.: US 8,961,928 B2
(45) Date of Patent: Feb. 24, 2015

(54) LIGAND AND METAL COMPLEX HAVING THE SAME

(75) Inventors: Yun-Ming Wang, Hsinchu (TW);
Gin-Chung Liu, Hsinchu (TW);
Chiao-Yun Chen, Hsinchu (TW);
Teng-Wen Li, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 73 days.

(21) Appl. No.: 13/467,471

(22) Filed: May 9, 2012

(65) Prior Publication Data
US 2013/0303728 A1   Nov. 14, 2013

(51) Int. Cl.
*A61K 51/00*   (2006.01)
*A61K 49/00*   (2006.01)
*A61B 5/00*   (2006.01)
*A61K 38/04*   (2006.01)

(52) U.S. Cl.
USPC ........... 424/1.69; 424/1.11; 424/9.1; 424/9.6; 530/327

(58) Field of Classification Search
CPC ....... C07K 7/08; A61K 49/06; A61K 49/101; A61K 49/14; A61K 38/00; A61K 51/088
See application file for complete search history.

(56) References Cited

U.S. PATENT DOCUMENTS

2011/0065905 A1*   3/2011   Wang et al. ............... 534/16

OTHER PUBLICATIONS

Lebel R., et al., "Novel Solubility-Switchable MRI Agent Allows the Noninvasive Detection of Matrix Metalloproteinase-2 Activity In Vivo in a Mouse Model", 2008, Mag. Res. Med., pp. 1056-1065.*
Bremer, C., et al., "Optical Imaging of Matrix Metalloproteinase-2 Activity in Tumors: Feasibility Study in a Mouse Model", 2001, Radiology, pp. 523-529.*
Chen et al., "Targeting of Matrix Metalloproteinase-2 activation with Gd-NBCB-TTDA-MMP-2 for detection of vulnerable atherosclerotic plaques using a novel molecular MR Imaging in vivo", Proc. Intl. Soc. Mag. Reson. Med., vol. 19 (May 10, 2011).

* cited by examiner

*Primary Examiner* — Michael G Hartley
*Assistant Examiner* — Lance Rider
(74) *Attorney, Agent, or Firm* — Mintz Levin Cohn Ferris Glovsky and Popeo, P.C.; Peter F. Corless; Richard B. Emmons

(57) ABSTRACT

A ligand and a metal complex having the ligand are provided. The ligand and a paramagnetic metal ion form a metal complex with high stability, high relaxivity and high biocompatibility. The metal complex of the present invention is applicable to the preparation of MRI contrast agents for detecting atherosclerosis. The MRI contrast agent includes a peptide sequence specific to a matrix metalloprotease, and can be recognized by a pathological thrombocyte to target a specific site, so as to enhance the imaging contrast.

15 Claims, 5 Drawing Sheets

(I)

(II)

(I)

(II)

LIGAND AND METAL COMPLEX HAVING THE SAME

FIELD OF INVENTION

The present invention relates to a ligand and a metal complex having the ligand, and more particularly, to a ligand having a peptide sequence specific to a matrix metalloprotease and a metal complex having the ligand.

BACKGROUND OF THE INVENTION

Magnetic resonance imaging contrast agents can be classified according to property at a magnetic field into the following: (1) $T_1$ contrast agents for reducing spin-lattice relaxation time $T_1$, and thereby increasing tissue signals; and (2) $T_2$ contrast agents for reducing spin-spin relaxation time $T_2$, and thereby reducing tissue signals and effectively identifying whether a tissue is normal (*J. Chem. Soc., Dalton Trans,* 1998, 4113-4118; *Helv. Chim. Acta,* 2002, 85, 1033).

A typical $T_1$ contrast agent is a metal complex having a paramagnetic metal ion and a plurality of ligands chelating the metal ion. A typical $T_2$ contrast agent is a polymer having nanoparticles such as superparamagnetic iron oxide nanoparticles (SPIO).

Currently, the magnetic resonance imaging technology has been used in animal models for producing images showing biochemical functions at molecular or cellular levels. There are many developments on contrast agents, especially on biomolecule-targeting contrast agents. Since cardiovascular diseases have higher incidence and mortality than tumors and are the most severe diseases, many magnetic resonance imaging contrast agents for detecting vascular thrombosis of atherosclerosis or cardiovascular diseases have been developed. For example, Chinese Patent No. 101347625 discloses MRI thrombus target-directed contrast agents and the preparation method thereof, wherein a P-selectin-targeting contrast agent ((Gd-DTPA)$_n$-BSA-PsL-EGFmAb) is provided for being coupled with epithermal growth factors (EGF) on thrombocytes. However, due to the large molecular weight, this contrast agent is not easy to enter an artery, and thus can only be used in the early stage of thrombosis. In addition, US Patent Application Publication No. 2011/0268663A discloses an intravascular contrast agent for MRI, wherein the contrast agent includes a Gd-complex attached with an amino acid unit. However, this contrast agent has poor specificity to thrombocytes, and is thus poorly identified by thrombocytes.

Matrix metalloproteases (MMPs) are proteases, and play important roles in physiology, pathology and structural construction, such as morphogenesis, angiogenesis, arthritis and tumor metastasis. It is found in the study of cardiovascular diseases that vascular smooth muscle cells move from an intermediate layer to an inner layer, and proliferate and accumulate at an inner layer of a blood vessel during atherosclerosis. While damages or thrombosis occurs at a blood vessel, matrix metalloprotease 2 are significantly expressed, and involves in the formation of atherosclerosis (*Physiol Rev,* 2005, 85, 1-31).

SUMMARY OF THE INVENTION

The present invention provides a ligand and a metal complex having the ligand, which can be identified and cleaved by an MMP and served as a targeting contrast agent to detect abnormal expressions of proteins, amino acids or receptors at the early stage of atherosclerosis. Accordingly, the ligand and the metal complex of the present invention provide early diagnosis, monitoring and treatment in the magnetic resonance imaging technology.

The present invention provides a ligand having the following structural formula (I):

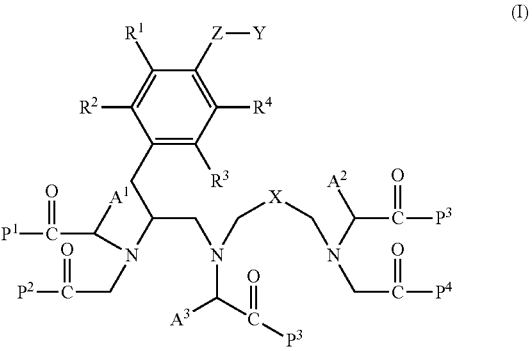

wherein $R^1$, $R^2$, $R^3$ and $R^4$ are independently hydrogen, nitro, amino or thiocyano; $P^1$, $P^2$, $P^3$, $P^4$ and $P^5$ are independently oxo, halo, hydroxyl or $C_{1-7}$alkyl; X is methylenyl, 1,1-cyclobutylenyl, 1,1-cyclopentylenyl or 1,1-cyclohexanylenyl; $A^1$, $A^2$ and $A^3$ are independently hydrogen, $C_{1-3}$alkyl, $C_{1-3}$-benzylalkyl, $C_{1-3}$-methoxybenzylalkyl, diphenylmethyl or $C_{1-3}$ isothiocyanobenzylalkyl; Z is a group binding to Y; and Y is an amino acid sequence comprising an MMP sequence.

The present invention further provides a metal complex, including a paramagnetic metal ion and a ligand chelating the paramagnetic metal ion.

Vascular thrombosis mainly results from atherosclerosis. In order to detect atherosclerosis, 3,6,10-tri-(carboxymethyl)-3,6,10-triazadodecanedioic acid (TTDA) is used as a base to be linked with functional groups, which increase water solubility and is specific to matrix metalloprotease 2, so as to form a ligand of the present invention.

Further, the ligand having a matrix metalloprotease 2 sequence is chelated with the paramagnetic metal ion to form a metal complex of the present invention. The metal complex can be used in the preparation of a magnetic resonance imaging contrast agent for detecting atherosclerosis.

Thus, in the present invention, TTDA is used as a base to form a ligand/metal complex. The ligand/metal complex is biocompatible with a target cell or tissue and can bind to the target cell or tissue. According to the present invention, the ligand/metal complex is specific to matrix metalloprotease 2 that is associated with atherosclerosis.

In the present invention, the matrix metalloprotease 2 sequence of the ligand/metal complex has an amino acid linker at the end, so as to increase water solubility before being cleaved by a matrix metalloprotease. Upon the cleavage by the matrix metalloprotease, the hydrophobicity of the matrix metalloprotease 2 sequence of the ligand/metal complex is increased so as to enhance the binding between the ligand/metal complex and human serum albumin (HSA). According to the present invention, the image contrast is enhanced and is beneficial for being used in a magnetic resonance imaging contrast agent.

BRIEF DESCRIPTION OF THE DRAWINGS

In FIGS. 3A and 3B, Lys×6 indicates that the MMP-2 sequence in the complex is linked to six lysines, Lys×3 indicates that the MMP-2 sequence in the complex is linked to three lysines; (I) shows the image result by using only the metal complex, (II) shows the image result by using the metal complex and MMP-2, (III) shows the image result by using the metal complex and HSA, and (IV) shows the image result by using the metal complex, HSA and MMP-2;

DETAILED DESCRIPTION OF THE PREFERRED EMBODIMENTS

Figure 1:
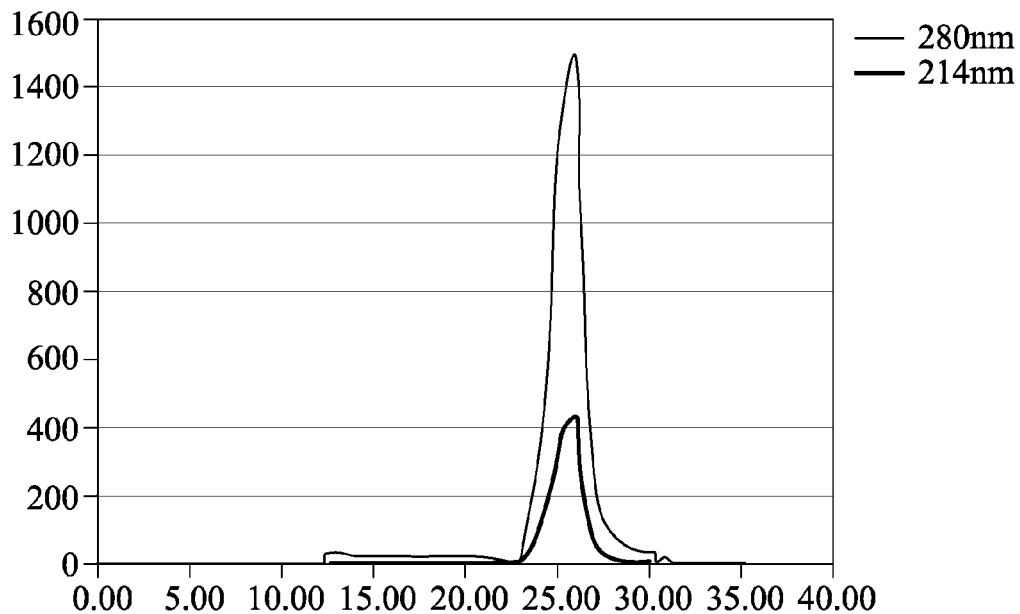
FIG. 1 shows the metal complex ([Gd(NBCB-TTDA-(L)-MMP-2)]$^{2-}$) of the present invention, wherein (I) shows the metal complex ([Gd(NBCB-TTDA-(L)-MMP-2)]$^{2-}$) before being cleaved by MMP-2, and (II) shows the metal complex ([Gd(NBCB-TTDA-(L)-MMP-2)]$^{2-}$) after being cleaved by MMP-2.
Figure 1:
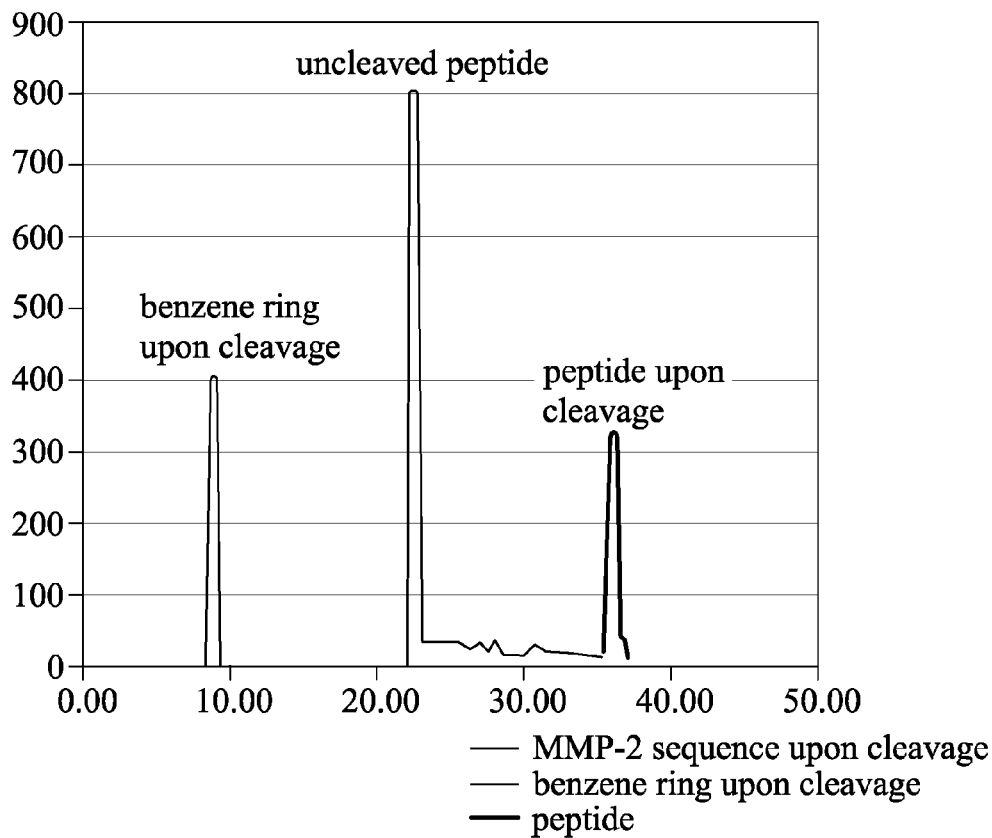

The following specific examples are used for illustrating the present invention. A person skilled in the art can easily conceive the other advantages and effects of the present invention.

The present invention provides a ligand having the following structural formula (I):

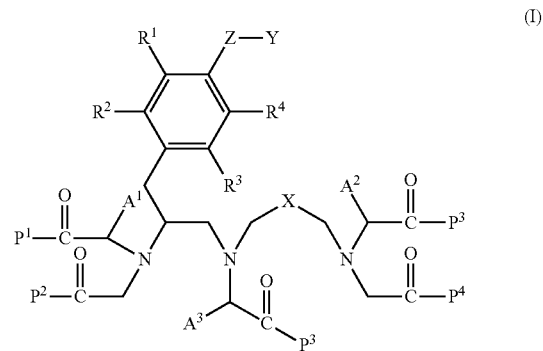

wherein $R^1$, $R^2$, $R^3$ and $R^4$ are independently hydrogen, nitro, amino or thiocyano; $P^1$, $P^2$, $P^3$, $P^4$ and $P^5$ are independently oxo, halo, hydroxyl or $C_{1-7}$alkyl; X is methylenyl, 1,1-cyclobutylenyl, 1,1-cyclopentylenyl or 1,1-cyclohexanylenyl; $A^1$, $A^2$ and $A^3$ are independently hydrogen, $C_{1-3}$alkyl, $C_{1-3}$-benzylalkyl, $C_{1-3}$-methoxybenzylalkyl, diphenylmethyl or $C_{1-3}$ isothiocyanobenzylalkyl; Z is a group binding to Y; and Y is an amino acid sequence comprising a matrix metalloprotease sequence. In one embodiment of the present invention, Y is an amino acid sequence comprising lysine.

In addition, the term "biocompatible molecule" herein refers to molecules compatible with cells or tissues (i.e., targets to be detected), such as peptides or antibodies. With regard to the targeting contrast agent, such molecule has to be coupled with the target cell or tissue.

In the formula (I), Z is

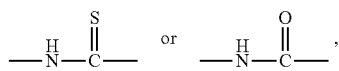

and Y is an amino acid sequence comprising a matrix metalloprotease 2 sequence. In one embodiment of the present invention, Y is an amino acid sequence comprising valine and lysine. In the present invention, valine is L-valine, and the ligand can thus be recognized by matrix metalloprotease 2.

In order to make the ligand of the present invention have more hydrophobicity and bind to human serum albumin as well as matrix metalloprotease 2, $A^1$, $A^2$ and $A^3$ may be optionally selected. Preferably, $A^1$, $A^2$ and $A^3$ are independently hydrogen, methyl, benzylmethyl, methoxybenzylmethyl, diphenylmethyl or $C_{1-3}$ isothiocyanobenzylalkyl.

In the ligand of formula (I), $P^1$, $P^2$, $P^3$, $P^4$ and $P^5$ are independently oxo, halo, hydroxyl or $C_{1-7}$alkyl, and preferably, hydroxyl or $C_{1-7}$alkyl.

In one embodiment, X is methylenyl. Also, each of $A^1$, $A^2$ and $A^3$ is hydrogen, and each of $R^1$, $R^2$, $R^3$ and $R^4$ is hydrogen.

In another embodiment, each of $R^1$, $R^2$, $R^3$ and $R^4$ is hydrogen. Also, X is 1,1-cyclobutylenyl, and each of $A^1$, $A^2$ and $A^3$ is hydrogen.

In accordance with the present invention, the ligand of formula (I) may be prepared by the conventional method for forming a ligand.

The present invention further provides a metal complex for a preparation of a magnetic resonance imaging contrast agent for detecting atherosclerosis. The metal complex of the present invention includes a paramagnetic metal ion and a ligand chelating the paramagnetic metal ion and having the structural formula (I), wherein $R^1$, $R^2$, $R^3$, $R^4$, $P^1$, $P^2$, $P^3$, $P^4$, $P^5$, X, $A^1$, $A^2$, $A^3$, $A^4$, Y and Z are defined as the above.

While the metal complex of the present invention is used to prepare a magnetic resonance imaging contrast agent for detecting atherosclerosis, the amino acid sequence including L-valine (hereinafter referred to (L)-MMP-2) that can be identified and cleaved by MMP-2. After the cleavage, the contrast agent has higher hydrophobicity, and thus accumulates at the pathological site, so as to achieve targeting contrast.

The amino acid sequence in the metal complex of the present invention is provided with lysine so as to increase hydrophilicity before cleavage, such that the hydrophilic magnetic resonance imaging contrast agent with low toxicity can be circulated to the tissue site of atherosclerosis via vascular injection. Then, the (L)-MMP-2 sequence in the metal complex of the present invention is recognized and cleaved by matrix metalloprotease 2. After cleavage, the hydrophobicity of (L)-MMP-2 is increased so as to facilitate the binding between (L)-MMP-2 and HSA, such that the image effect is significantly improved. Further, 95% of the injected MRI contrast agents prepared by the metal complex of the present invention are washed out from the body in 24 hours.

In the metal complex of the present invention, the paramagnetic metal ion may be any metal ion for the magnetic resonance imaging technology which is nontoxic to an organism. In an embodiment of the present, the metal complex has the following structural formula (II):

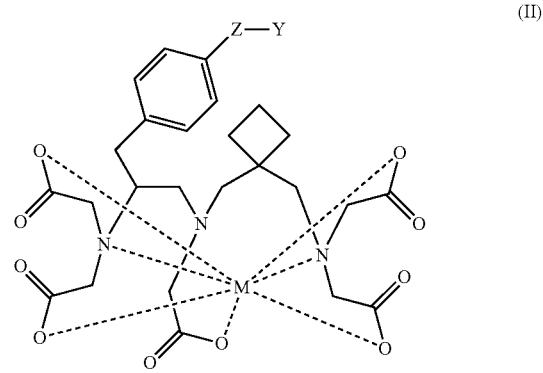

(II)

wherein M is a metal ion, Z is

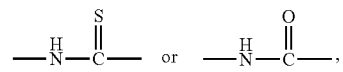

and Y is an amino acid sequence comprising a matrix metalloprotease 2 sequence. In one embodiment of the present invention, the amino acid sequence of Y comprises valine and lysine. In one embodiment of the present invention, the amino acid sequence of Y comprises L-valine, and can be recognized by matrix metalloprotease 2.

Preferably, the metal ion may be a lanthanide metal ion, a manganese ion or an iron ion. More preferably, the metal ion may be $Gd^{3+}$, $Mn^{2+}$ or $Fe^{3+}$. In one embodiment of the present invention, the metal ion is $Gd^{3+}$.

In the present invention, Y has the following structural formula (III):

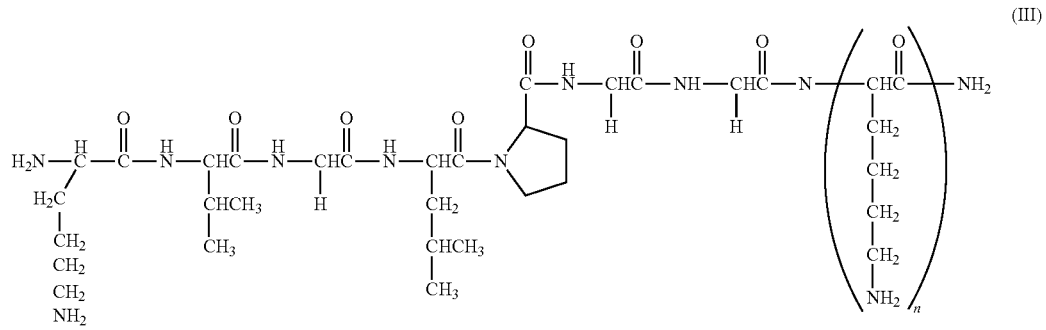

(III)

wherein n is an integer in a range from 2 to 8, and preferably in a range from 3 to 6.
In one embodiment of the present invention, Y is presented as the following structural formula (III-1):
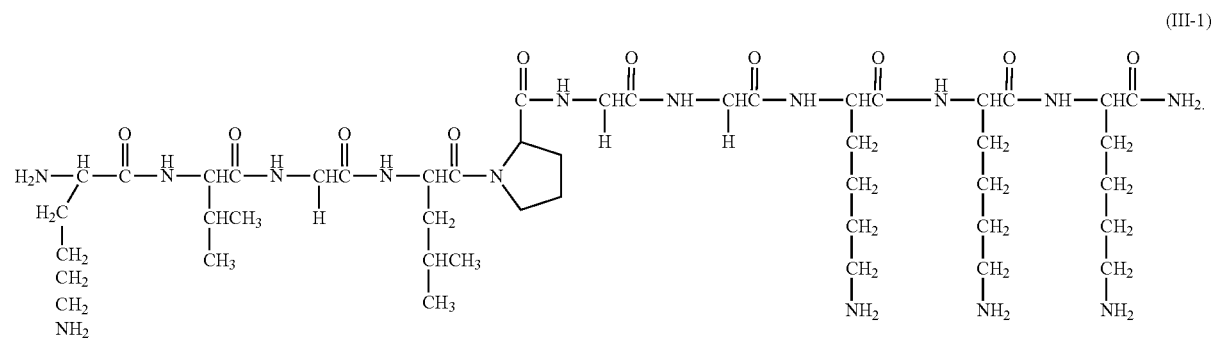
In another embodiment of the present invention, Y is presented as the following structural formula (III-2):

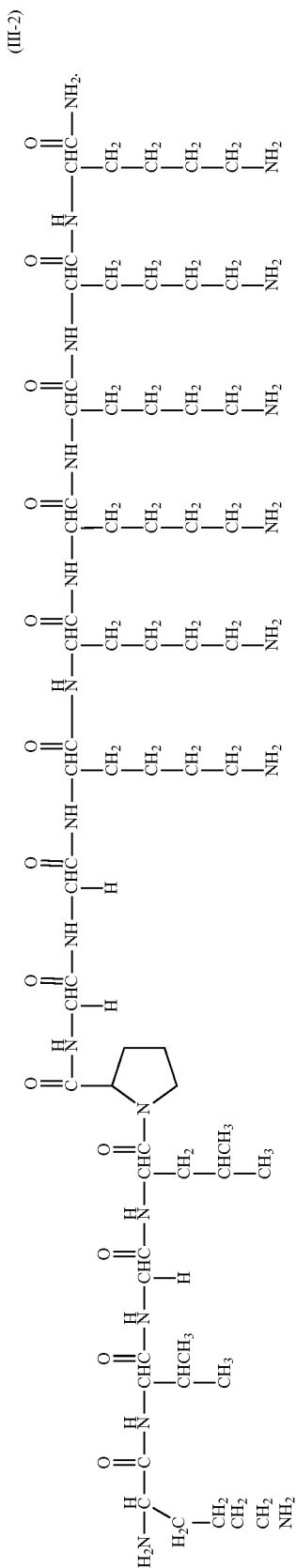
(III-2)

The metal complex of the present invention can be used to prepare a magnetic resonance imaging contrast agent for detecting atherosclerosis, and the amino acid sequence of Y is used as a targeting peptide sequence.

In one embodiment of the present invention, the metal complex has the following structural formula (VI):

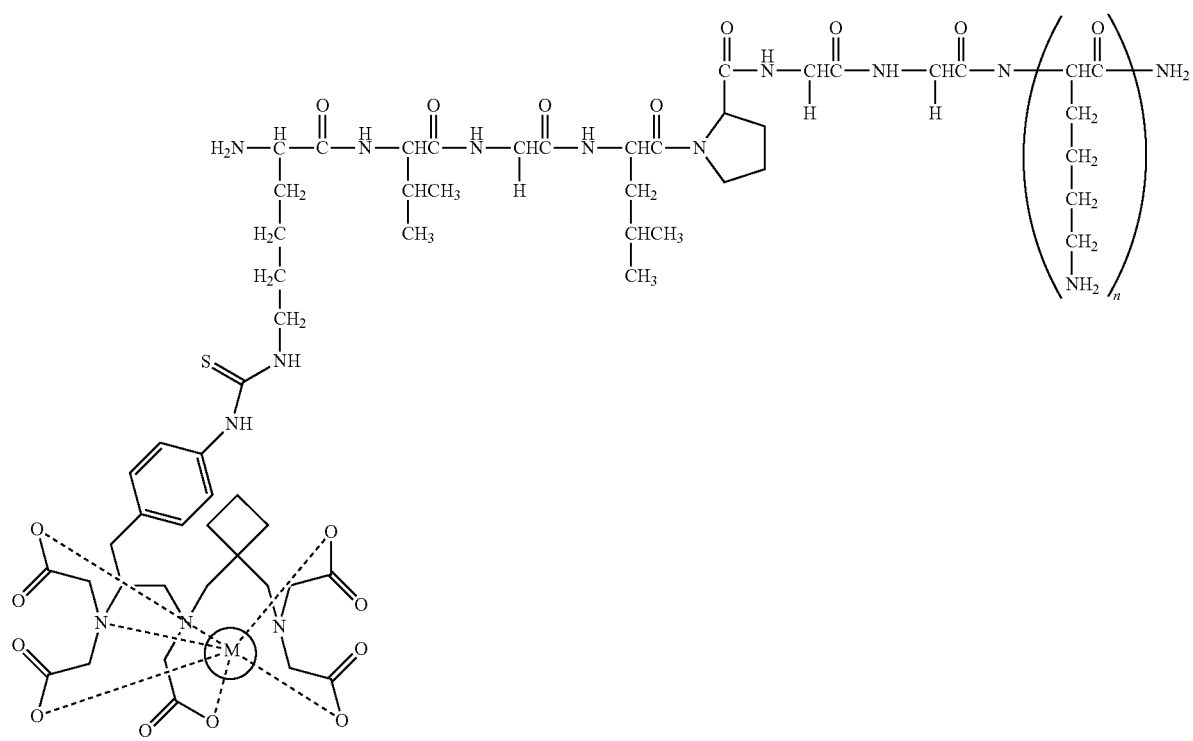

(IV)

wherein M is $Gd^{3+}$, $Mn^{2+}$ or $Fe^{3+}$, and n is an integer in a range from 2 to 8.

In one embodiment of the present invention, $Gd^{3+}$ is used as the metal ion, and the metal complex has the following structural formula (V):

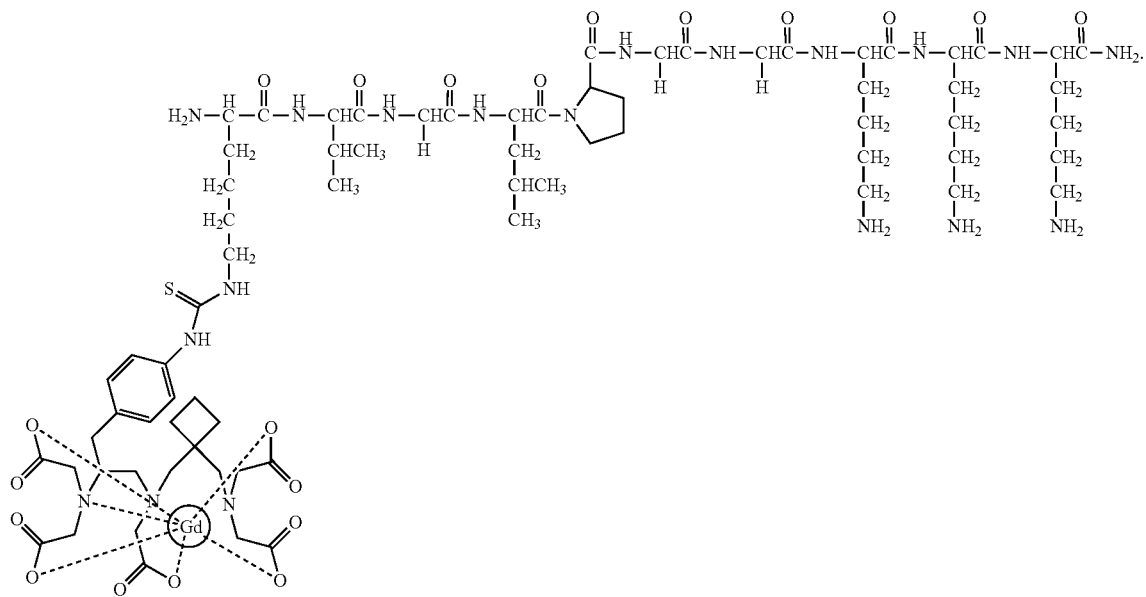
(V)
In another embodiment of the present invention, $Gd^{3+}$ is used as the metal ion, and the metal complex has the following structural formula (VI):

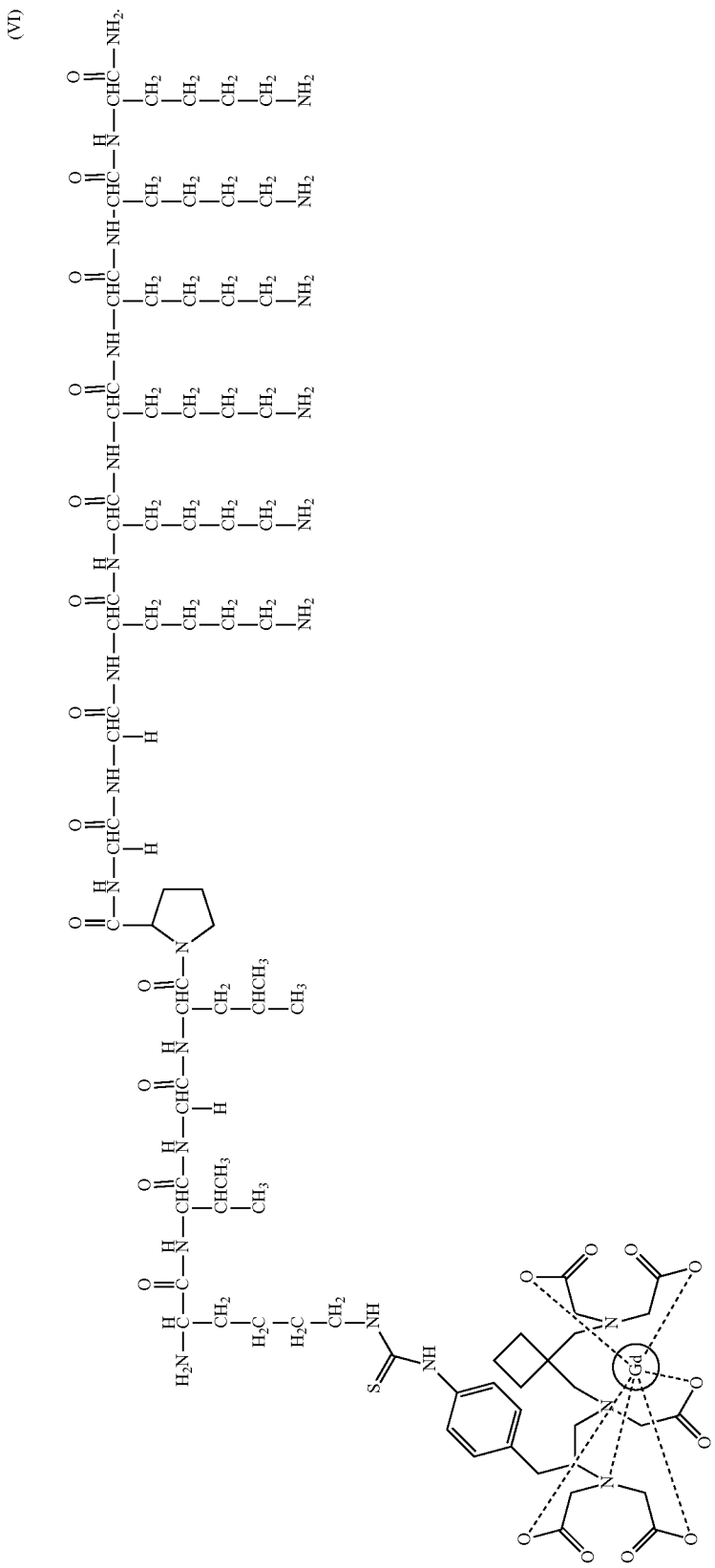

It is found that the metal complex of the present invention has great relaxivity and significant binding to HSA, and thus provides outstanding results in the MR image study. Hence, the metal complex of the present invention is applicable to a preparation of a magnetic resonance imaging contrast agent for detecting atherosclerosis.

The following embodiments are used for illustrating features and effects of the present invention, but not for limiting the scope of the present invention.

Embodiments

The products prepared from each of the steps were identified by $^1$H-NMR, $^{13}$C-NMR, a mass spectrometer and the elemental analysis.

Preparation 1: Preparation of NBCB-TTDA

1.1 Synthesis of C-(1-aminomethyl-cyclobutyl)-methylamine

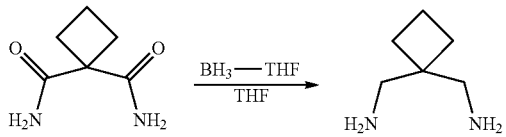

Cyclobutane-1 μl-dicarboxylic acid diamine (5.2 g, 36.6 mol), 250 ml of anhydrous tetrahydrofuran and 300 ml of 1M borane-tetrahydrofuran (BH$_3$:THF=1:8 (mole ratio)) were mixed in the ice bath under nitrogen to form a reaction solution. The reaction of the solution was performed in the ice bath for 1 hour, heated to 70° C. for 36 hours, and then stopped by addition of methanol. Then, the solvent of the reaction solution was removed by a rotary evaporator, so as to obtain a crude product.

The crude product, 250 ml of ethanol and 50 ml of 6N HCl were mixed to form a mixture. The mixture was heated to 80°, and refluxed for 12 hours. Upon the reaction, the solvent of the mixture was removed by a rotary evaporator, so as to obtain yellow oil. The yellow oil was added with water, and the pH of the oil was adjusted to 2 by HCl. Then, the yellow oil was placed in 100 ml of AG 50 W×8 cation exchange resin (purchased from Aldrich, 200-400 mesh, H$^+$ type resin) column (3×20 cm). The column was eluted with different concentrations (0.5 to 3.0 N) of HCl solution, and the eluates were collected separately to be identified by $^1$H-NMR, $^{13}$C-NMR, a mass spectrometer and the elemental analysis. The eluates of 1.0 to 2.0 N HCl solution were collected to be concentrated, so as to obtain 3.0 g (26.3 mmol, yield: 70.9%) of C-(1-aminomethyl-cyclobutyl)-methylamine.

The result of the analysis was: $^1$H-NMR (D$_2$O, 400 MHz), □ (ppm): 2.95 (s, 4H, NH$_2$CH$_2$CCH$_2$NH$_2$), 1.87-1.81 (m, 6H, CCH$_2$CH$_2$CH$_2$); $^{13}$C-NMR (D$_2$O, 100 MHz), □ (ppm): 49.93, 49.81, 36.91, 27.73, 26.28, 14.46; ESI-MS (m/z): 114.19 (calculation value), 114.76 [M+H]$^+$ (experimental value); analysis value (experimental value) of C$_6$H$_{14}$N$_2$.3HCl: C, 32.44 (32.23); H, 7.20 (7.66); N, 12.24 (12.53).

1.2 Synthesis of L-nitrophenylalanine methyl ester

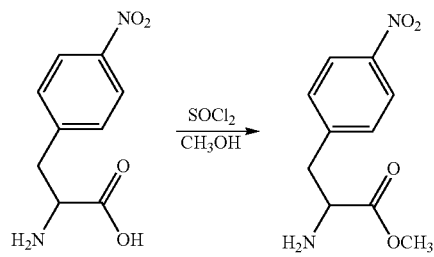

SOCl$_2$ (2.9 g) of was added with 40 ml of methanol and stirred for 30 minutes in the ice bath, and then mixed with 5.1 g of L-nitroaniline, so as to form a reaction solution. The reaction solution was heated to 70° C., and refluxed for 24 hours. After the reaction, the solvent of the reaction solution was removed by a rotary evaporator, then recrystallized with ether, filtered and dried, so as to obtain 5.3 g (yield: 97.1%) of a white solid, L-nitrophenylalanine methyl ester.

The result of the analysis was: ESI-MS: m/z 224.21 (calculation value), 224.81 [M+H]$^+$ (experimental value). Anal. Calcd (Found) for C$_{10}$H$_{12}$N$_2$O$_4$.HCl: C, 45.88 (45.51); H, 5.03 (5.05); N, 10.75 (10.74). $^1$H NMR (DMSO, 400 MHz), δ (ppm): 8.80 (s, 2H, —NH2), 8.22-8.18 (d, 2H, NO$_2$CCH$_2$), 7.59-7.55 (d, 2H, NO$_2$CCH$_2$CH$_2$), 4.37 (t, 1H, NH$_2$CH), 3.68 (s, 3H, OCH$_3$), 3.36 (m, 2H, CH$_2$Ar). $^{13}$C NMR (DMSO, 100 MHz), δ (ppm): 169.04, 146.83, 143.11, 131.01, 123.59, 52.74, 52.71, 35.31.

1.3 Synthesis of 2-amino-N-((1-(aminomethyl)cyclobutyl)methyl)-3-(4-nitrophenyl)-propanamide

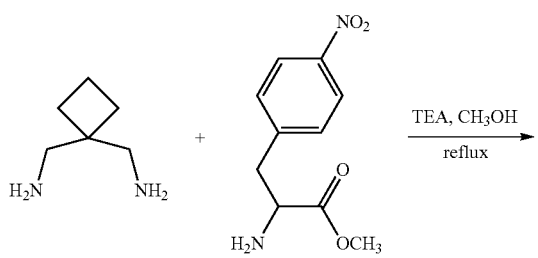

-continued

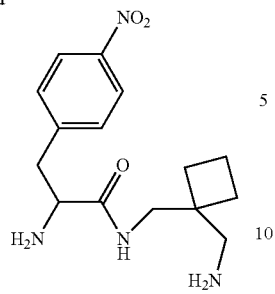

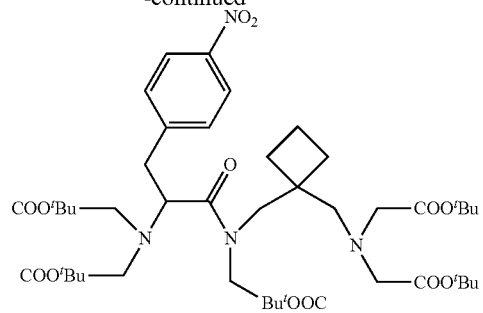

C-(1-aminomethyl-cyclobutyl)-methylamine (2.4 g, 20.6 mmol) of was mixed with 100 ml of methanol, and then the pH of the mixture was adjusted to 9-10 with triethylamine, so as to obtain a first reaction solution. 4.2 g (18.6 mmol) of L-nitrophenylalanine methyl ester was mixed with 100 ml of methanol, so as to obtain a second reaction solution. The second reaction solution was dropped into the first reaction solution, so as to obtain a mixed solution. The mixed solution was heated to 60° C. to 70°, and refluxed for 19 hours. After the reaction, the solvent of the mixed solution was removed by a rotary evaporator, so as to obtain a crude product.

The crude product was dissolved with an ammonia solution, and extracted with chloroform and water. Then, the organic layer was collected. The solvent of the organic layer was removed by a rotary evaporator, so as to obtain 2.9 g (9.4 mmol, yield: 50.4%) of light yellow oil, 2-amino-N-((1-(aminomethyl)cyclobutyl)methyl)-3-(4-nitrophenyl)-propanamide.

The result of the analysis was: ESI-MS: m/z 306.17 (calculation value), 307.13 [M+H]$^+$ (experimental value). Anal. Calcd (Found) for $C_{15}H_{22}N_4O_3 \cdot 2HCl \cdot H_2O$: C, 45.70 (45.35); H, 6.66 (6.60); N, 13.80 (14.10). $^1$H NMR ($D_2O$, 400 MHz), δ (ppm): 8.17-8.15 (d, 2H, $NO_2CCH_2$), 7.46-7.44 (d, 2H, $NO_2CCH_2CH_2$), 4.26-4.23 (t, 1H, $NH_2CH$), 3.31-3.15 (m, 4H, —$NCH_2CCH_2NH_2$), 2.82-2.61 (m, 2H, $CH_2Ar$), 1.76-1.57 (m, 6H, —$CCH_2CH_2CH_2$—). $^{13}$C NMR ($D_2O$, 100 MHz), δ (ppm): 169.83, 147.39, 142.04, 130.72, 124.37, 54.04, 44.42, 43.45, 40.19, 36.72, 26.88, 26.61, 14.11. 4.

1.4 Synthesis of 4-nitrobenzyl-8-cyclobutyl-3,6,10-tri-(carboxymethyl)-3,6,10-tetraazacylodecyl (NBCB-TTDA(Bu$^t$))

31.2 ml of 1M borane-tetrafuran [$BH_3$:THF=1:4 (mole ratio)] was dropped into 2.4 g (7.8 mmol) of 2-amino-N-((1-(aminomethyl)cyclobutyl)methyl)-3-(4-nitrophenyl)-propanamide in the ice bath under nitrogen, so as to obtain a reaction solution. The reaction of the solution was performed in the ice bath for 1 hour, then removed from the ice bath, and heated to 70°. Then, the reaction was performed for 36 hours. The reaction solution was then added with methanol, and then the methanol was removed by a rotary evaporator. The reaction solution was added with 50 ml of ethanol and 10 ml of 6N HCl. The mixture was heated to 80° C., and refluxed for 12 hours. The solvent of the mixture was then removed by the rotary evaporator, dissolved with an ammonia solution, and extracted with chloroform and water. Then, the organic layer was collected, and the solvent of the organic layer was removed by the rotary evaporator, so as to obtain 1.9 g of yellow oil.

The yellow oil was dissolved in 250 ml of acetonitrile, and added with 8.0 g (57.8 mmol) potassium carbonate. The pH of the mixture was kept at about 10. Then, the mixture was added with 6.1 ml (42.4 mol) of $BrCH_2COO^tBu$, so as to obtain a reaction solution. The reaction solution was heated and refluxed at 70° for 48 hours. The reaction solution was filtered and concentrated, and then extracted with chloroform and water. The chloroform layer was collected, concentrated, and purified by silica gel column chromatography. The column was eluted with dichloromethane/methanol (dichloromethane:methanol=39:1). The eluate was collected, concentrated and dried, so as to obtain 3.4 g (3:9 mmol, yield: 50.0%) of yellow oil, NBCB-TTDA(tert).

The result of the analysis was: ESI-MS (m/z): 863.80 (calculation value), 863.56 [M+H]$^+$ (experimental value).

1.5 Synthesis of 4-aminobenzyl-8-cyclobutyl-3,6,10-tri-(carboxymethyl)-3,6,10-tetraazacylodecyl (NBCB-TTDA(NH$_2$))

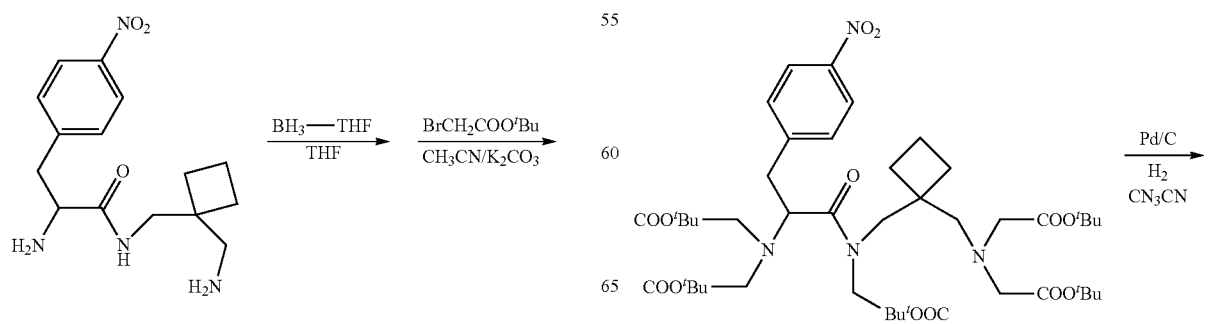

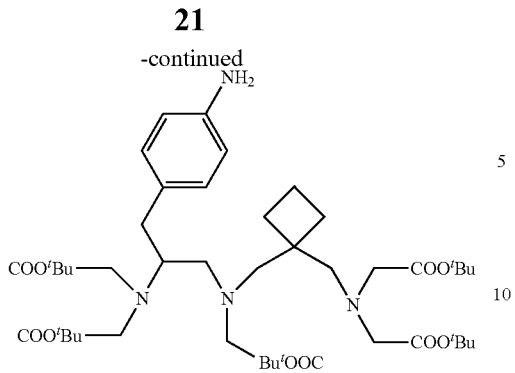

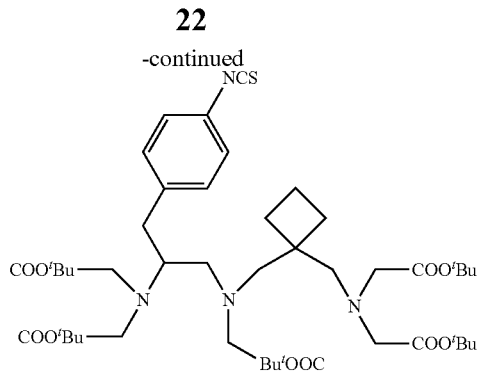

100 mg of palladium on charcoal was added into 4-nitrobenzyl-8-cyclobutyl-3,6,10-tri-(carboxymethyl)-3,6,10-triisobutylacetyl as a catalyst, and then dissolved in $CH_3CH$, so as to obtain a reaction solution. The reaction solution was placed in a flask under vacuum, and then hydrogen was introduced. The reaction was performed at 2 atm, and hydrogen was continuously introduced while the pressure decreased. After the reaction, the palladium on charcoal was filtered and removed, and the solvent of the reaction solution was removed by the rotary evaporator, so as obtain the yellow oil.

The yellow oil was purified by a silica gel column chromatography. The column was eluted with dichloromethane/methanol (dichloromethane:methanol=39:1). The eluate was collected, concentrated and dried, so as to obtain 1.4 g (1.7 mmol, yield: 60.7%) of yellow oil, $NBCB-TTDA-NH_2$.

The result of the analysis was: ESI-MS (m/z): 833.88 (calculation value), 833.44 $[M+H]^+$ (experimental value).

4-aminobenzyl-8-cyclobutyl-3,6,10-tri-(carboxymethyl)-3,6,10-triisobutylacetyl (5.2 g, 2.4 mmol) was dissolved in 200 ml of dichloromethane, added with 5 ml of triethylamine, and then added with 276 mg (2.4 mmol) of thiophosgene ($CSCl_2$). The reaction was performed in dark for 12 hours. After the reaction, the mixture was extracted with dichloromethane and water. Then, the organic layer was collected, and the solvent in the organic layer was removed by the rotary evaporator, so as to obtain 1.9 g of red oil, a crude product.

The red oil was purified by a silica gel column chromatography. The column was eluted with dichloromethane/methanol (dichlormethane:methanol=39:1). The eluate was collected, and dried by the rotary evaporator, so as to obtain 1.4 g (1.6 mmol, yield: 66.7%) of yellow oil, NBCB-TTDA (NCS).

The result of the analysis was: ESI-MS (m/z): 875.34 (calculation value), 875.7 $[M+H]^+$ (experimental value).

Preparation 2: Preparation of a Matrix Metalloprotease 2 Sequence 2.1 Preparation of (L)-MMP-2 sequence

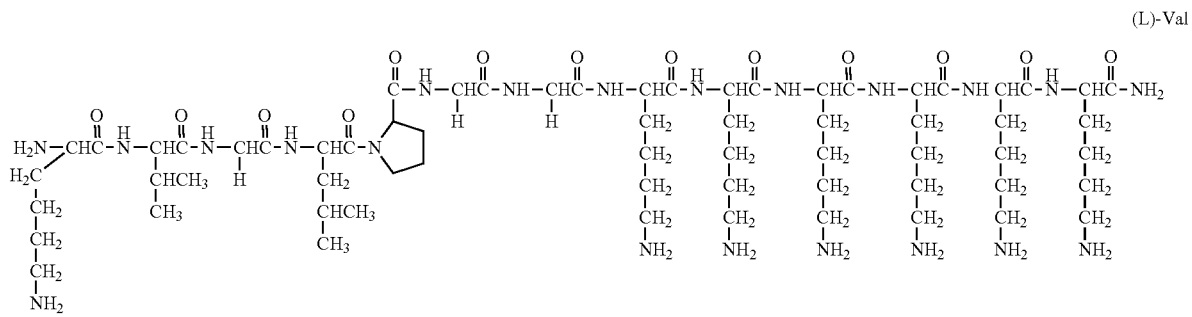

1.6 Synthesis of 4-sulfur cyano benzyl-8-cyclobutyl-3,6,10-tri-(carboxymethyl)-3,6,10-tetraazacyclodecyl (NBCB-TTDA(NCS))

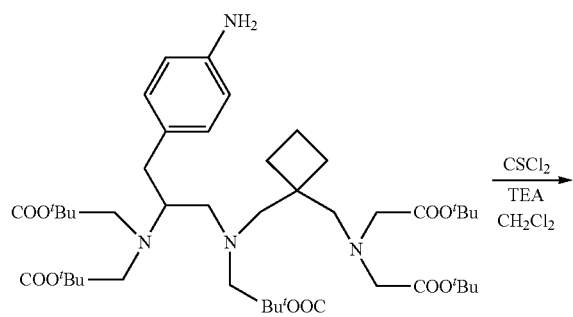

0.5 g (0.31 mmol) of resin (Rink Amide resin from Novabiochem, 100-200 mesh) was placed in 0.4 M NMM/DMF solution in a PS3 reaction flask, and added with amino acids, benzotriazole-1-yl-oxy-tris-pyrrolidino-phosphonium hexafluorophosphate (PyBOP) and N-hydroxybenzotriazole.$H_2O$(HOBT). After the reaction, a Kaiser test was performed, in which the solvent being black indicated that the protecting groups on the resin were removed, and the solvent being yellow indicated that the protecting groups on the resin were not completely removed and further needed to be removed. Once an amino acid was synthesized on the amino acid sequence, the N-terminals on the resin which were not attached to amino acids reacted with acetaldehyde, such that the N-terminals on the resin would not react with a carboxylic group while attaching the next amino acid, so as to facilitate the purification of the peptide.

The above procedure was repeated, so as to synthesize amino acid sequences having three lysines and six lysines, which changed hydrophobicity of the amino acid sequence.

ESI-MS (m/z): 1395.78 (calculation value), 1396.8 [M+H]⁺ (experimental value).

2.2 Preparation of (D)-MMP-2 sequence

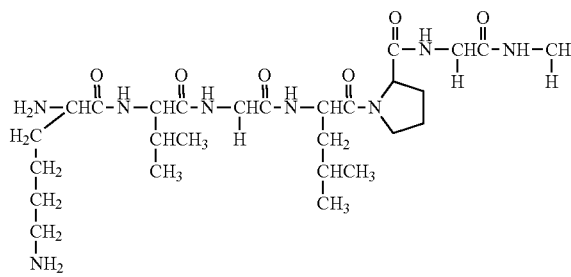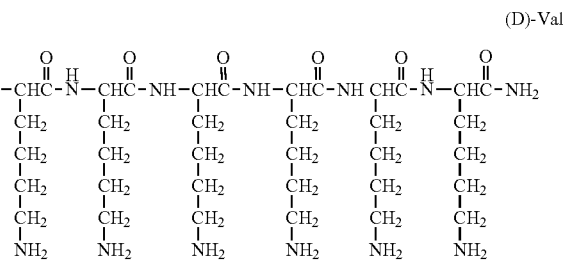

0.5 g (0.31 mmol) of resin (Rink Amide resin from Novabiochem, 100-200 mesh) was placed in 0.4 M NMM/DMF solution in a PS3 flask, and added with amino acids, benzotriazole-1-yl-oxy-tris-pyrrolidino-phosphonium hexafluorophosphate (PyBOP) and N-Hydroxybenzotriazole.H₂O (HOBT). After the reaction, a Kaiser test was performed, in which the solvent being black indicated that the protecting groups on the resin were removed, and the solvent being yellow indicated that the protecting groups on the resin were not completely removed and further needed to be removed. Once an amino acid was synthesized on the amino acid sequence, the N-terminals on the resin which were not attached to amino acids reacted with acetaldehyde, such that the N-terminals on the resin would not react with a carboxylic group while attaching the next amino acid, so as to facilitate the purification of the peptide. The above procedure was repeated, so as to change the L-valine at the terminal of the amino acid sequence to D-valine, which cannot be recognized by MMP-2. The (D)-MMP-2 sequence was used as the Comparative Example in the present invention.

ESI-MS (m/z): 1395.78 (calculation value), 1396.8 [M+H]⁺ (experimental value).

Preparation 3: Preparation of a Ligand Having the Structural Formula (I)

3.1 Preparation of a ligand NBCB-TTDA-(L)-MMP-2 Having the Structural Formula (I)

0.72 g (0.822 mmol) of NBCB-TTDA(NCS) and 0.5 g (0.31 mmol) of the resin attached with the (L)-MMP-2 sequence were placed in a PS3 flask, and added with 10 ml of DMSO and 5 ml of DIPEA. The reaction was performed at 25° C. for 24 hours. After the reaction, 0.5 g of the reacted resin and 10 ml of a cleaving reagent and a protecting group removing solvent (mixture of trifluoroacetic acid, deionized water and triethylsilicane (volume ratio: 95:2.5:2.5)) were stirred and mixed for 1.5 hour. Then, the reacted resin was washed with methanol and toluene and then filtered. The filtrate was collected and added with triethylamine to neutralize trifluoroacetic acid. The solvent in the filtrate was removed by the rotary evaporator, and then the ice ether was dropped into the filtrate to form a mixture. The mixture was centrifuged by a centrifuge for 5 minutes (1500 rpm). The mixture was formed into a solid layer and a liquid layer, and then repeatedly washed with ether until the upper layer was colorless and clear. The upper layer was collected by a dropper, placed in a centrifuge tube, added with deionized water, frozen in a refrigerator, and freeze-dried, so as to obtain a white powder, a crude product. Then, the crude product was purified by liquid chromatography to form NBCB-TTDA-(L)-MMP-2.

ESI-MS (m/z): 1990.41 (calculation value), 1991.5 [M+H]⁺ (experimental value).

3.2 Preparation of a ligand NBCB-TTDA-(D)-MMP-2 of the Comparative Example 0.72 g (0.822 mmol) of NBCB-TTDA(NCS) and 0.5 g (0.31 mmol) of the resin attached with the (D)-MMP-2 sequence were placed in a PS3 flask, and added with 10 ml of DMSO and 5 ml of DIPEA. The reaction was performed at 25° C. for 24 hours. After the reaction, 0.5 g of the reacted resin and 10 ml of a cleaving reagent and a protecting group removing solvent (mixture of trifluoroacetic acid, deionized water and triethylsilicane (volume ratio: 95:2.5:2.5)) were stirred and mixed for 1.5 hour. Then, the reacted resin was washed with methanol and toluene and then filtered. The filtrate was collected and added with triethylamine to neutralize trifluoroacetic acid. The solvent in the filtrate was removed by the rotary evaporator, and then ice ether was dropped into the filtrate to form a mixture. The mixture was centrifuged by a centrifuge for 5 minutes (1500 rpm). The mixture was formed into a solid layer and a liquid layer, and then repeatedly washed with ether until the upper layer was colorless and clear. The upper layer was collected by a dropper, placed in a centrifuge tube, added with deionized water, frozen in a refrigerator, and freeze-dried, so as to obtain a white powder, a crude product. Then, the crude product was purified by liquid chromatography to form NBCB-TTDA-(D)-MMP-2.

ESI-MS (m/z): 1990.41 (calculation value), 1991.5 [M+H]⁺ (experimental value).

Preparation 4: Preparation of a Metal Complex Having the Structural Formula (IV)

4.1 Preparation of a Metal Complex Gd(NBCB-TTDA-(L)-MMP-2)]²⁻

0.2 mmol of the ligand NBCB-TTDA-(L)-MMP-2 prepared from Preparation 3.1 and 0.198 mmol of gadolinium chloride were mixed, and then added with 5 ml of deionized water, so as to form a reaction solution. The reaction of the solution was performed at room temperature for 48 hours, and then stopped. The reaction solution was frozen, removed by a freeze-drying system (LABCONCO), and analyzed by liquid chromatography (Amersham Biosciences). The analyzed solution was collected and identified by a mass spectrometer. The collected solution was frozen, and treated by a freeze-drying system to remove the reaction solvent, so as to obtain a white powder, [Gd(NBCB-TTDA-(L)-MMP-2)]$^{2-}$.

ESI-MS (m/z): 2142.62 (calculation value), 2143.8 [M+H]$^+$ (experimental value).

4.2 Preparation of a Metal Complex Gd(NBCB-TTDA-(D)-MMP-2)]$^{2-}$ of the Comparative Example 0.2 mmol of the ligand NBCB-TTDA-(D)-MMP-2 prepared from Preparation 3.2 and 0.198 mmol of gadolinium chloride were mixed, and then added with 5 ml of deionized water, so as to form a reaction solution. The reaction of the solution was performed at room temperature for 48 hours, and then stopped. The reaction solution was frozen, removed by a freeze-drying system (LABCONCO), and analyzed by liquid chromatography (Amersham Biosciences). The analyzed solution was collected and identified by a mass spectrometer. The collected solution was frozen, and treated by a freeze-drying system to remove the reaction solvent, so as to obtain a white powder, [Gd(NBCB-TTDA-(6)-MMP-2)]$^{2-}$.

ESI-MS (m/z): 2142.62 (calculation value), 2143.8 [M+H]$^+$ (experimental value).

Measurement

The metal complexes prepared from Preparations 1 and 2 were studied and the results were shown as follows.

Study 1: Relaxivity ($r_1$) Measurement

Longitudinal relaxivity ($r_{1P}$) is constituted of inner relaxivity ($R_{1p}^{is}$) and outer relaxivity ($R_{1p}^{is}$) as shown in the following equation (iii):

$$r_{1p} = R_{1p}^{is} + R_{1p}^{os} \quad \text{(iii)}$$

For the Gd complex, the outer relaxivity was shown as the following equation (iv):

$$R_{1p}^{os} = C^{os}\left(\frac{1}{aD}\right)[7J(\omega_S) + 3J(\omega_H)] \quad \text{(iv)}$$

$C^{os}$ was a constant ($5.8 \times 10^{-13}$ S$^{-2}$M$^{-1}$), a was the minimal distance between the metal and the H$_2$O molecule, D was a solute-solvent diffusion coefficient and $J(\omega_i)$ (i=S and H) was non-Lorentzian spectral density function. For Gd complexes with similar sizes, the outer relaxivity may be assumed to be similar. Therefore, the relaxivity was mainly contributed from the inner relaxivity. The inner relaxivity was calculated according to the following equation (v):

$$R_{1p}^{is} = [C]q/[55.6(T_{1M} + \tau_M)] \quad \text{(v)}$$

[C] was the molar concentration of the Gd complex, q was the number of H$_2$O molecules bound to the metal ion, $T_{1M}$ was the longitudinal relaxivity time of the inner layer of H$_2$O molecules, and $\tau_M$ was the water residence life time of the inner layer of H$_2$O molecules.

The metal complex (having 6 lysines) [Gd(NBCB-TTDA-(L)-MMP-2)]$^{2-}$ having the structural formula (VI) was calculated according to the above equation. The study result were shown in Table 1. (The data of [Gd(TTDA)]$^{2-}$ were derived from Inorg. Chem., 2005, 44, 382, and the data of [Gd(DTPA)]$^{2-}$ were derived from Inorg. Chem., 2001, 40, 2170-2176.)

TABLE 1

Study and calculation result of [Gd(NBCB-TTDA-(L)-MMP-2)]$^{2-}$

| Metal complex | pH | Relaxivity $r_1$(mM$^{-1}$ s$^{-1}$) |
|---|---|---|
| [Gd(NBCB-TTDA-(L)-MMP-2)]$^{2-}$ | 7.4 ± 0.1 | 5.29 ± 0.03 |
| [Gd(TTDA)]$^{2-}$ | 7.5 ± 0.1 | 3.85 ± 0.03 |
| [Gd(DTPA)]$^{2-}$ | 7.6 ± 0.1 | 3.89 ± 0.03 |

As shown in Table 1, [Gd(NBCB-TTDA-(L)-MMP-2)]$^{2-}$ has higher relaxivity than those of [Gd(CB-TTDA)]$^{2-}$ and [Gd(TTDA)]$^{2-}$. In other words, both benzyl and cyclobutyl were introduced in the structure to increase the molecular weight and relaxivity.

In addition, [Gd(NBCB-TTDA)]$^{2-}$ has higher relaxivity than that of the commercial contrast agent [Gd(DTPA)]$^{2-}$. Accordingly, the relaxivity of the metal complex of the present invention meets the requirements for the commercial contrast agents to be used for MRI contrast agents.

Similarly, the metal complex having the structural formula (V) of the present invention meets the relaxivity required by the commercial contrast agents.

Study 2: Study of Specificity to MMP-2

1. Study of the Metal Complex [Gd(NBCB-TTDA-(L)-MMP2)]$^{2-}$ having the Structural Formula (VI) by High Performance Liquid Chromatography 0.2 mg of [Gd(NBCB-TTDA-(L)-MMP-2)]$^{2-}$ (dissolved in 200 µl of PBS (0.5 mM)) was added with MMP-2 (purchased from SIGMA), the reaction was performed for 30 minutes, and then HSA (purchased from SIGMA) was added into the reaction to react for 30 minutes. Then, the mixture was purified and analyzed by high performance liquid chromatography (Amersham ÄKTAbasic 10). In the HPLC analysis, the mobile phase was 100% CH$_3$OH, the flow rate was 1 ml/min, and the UV/vis detection wavelengths were 214 nm and 280 nm. The result was shown in FIG. 1.

2. Study of the Metal Complex [Gd(NBCB-TTDA-(D)-MMP2)]$^{2-}$ of the Comparative Example by High Performance Liquid Chromatography 0.2 mg of [Gd(NBCB-TTDA-(D)-MMP-2)]$^{2-}$ (dissolved in 200 µl of PBS (0.5 mM)) was added with MMP-2 (purchased from SIGMA), the reaction was performed for 30 minutes, and then HSA (purchased from SIGMA) was added into the reaction to react for 30 minutes. Then, the mixture was purified and analyzed by high performance liquid chromatography (Amersham ÄKTAbasic 10). In the HPLC analysis, the mobile phase was 100% CH$_3$OH, the flow rate was 1 ml/min, and the UV/vis detection wavelengths were 214 nm and 280 nm. The result was shown in FIG. 2.

Figure 2:
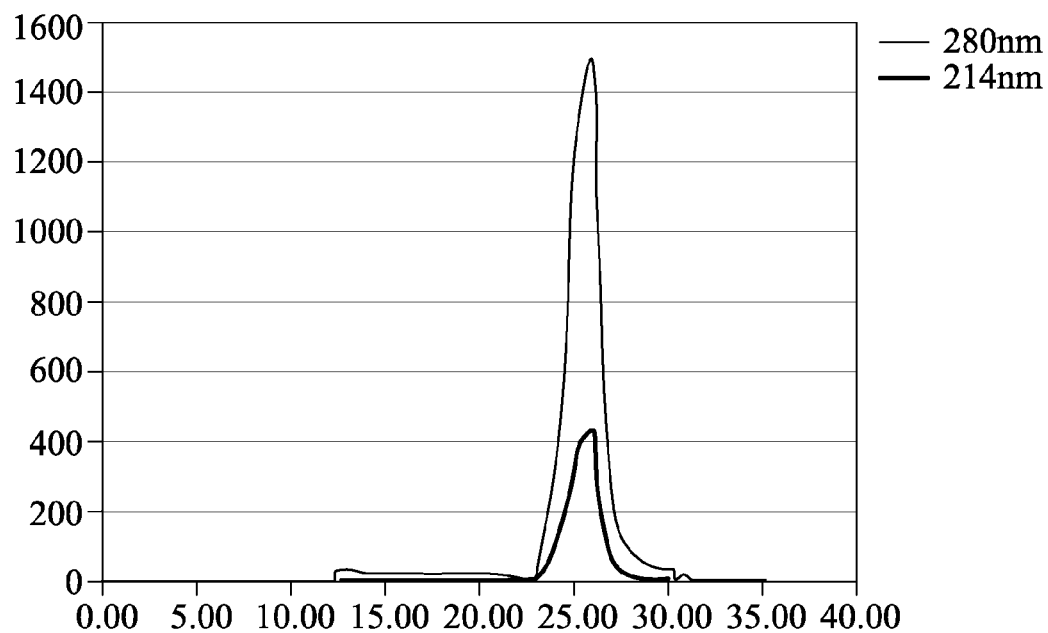
FIG. 2 shows the metal complex ([Gd(NBCB-TTDA-(D)-MMP-2)]$^{2-}$) of the Comparative Example, wherein (I) shows the metal complex ([Gd(NBCB-TTDA-(D)-MMP-2)]$^{2-}$) before adding MMP-2, and (II) shows the result after adding MMP-2, in which the metal complex ([Gd(NBCB-TTDA-(D)-MMP-2)]$^{2-}$) is not cleaved by MMP-2.
Figure 2:
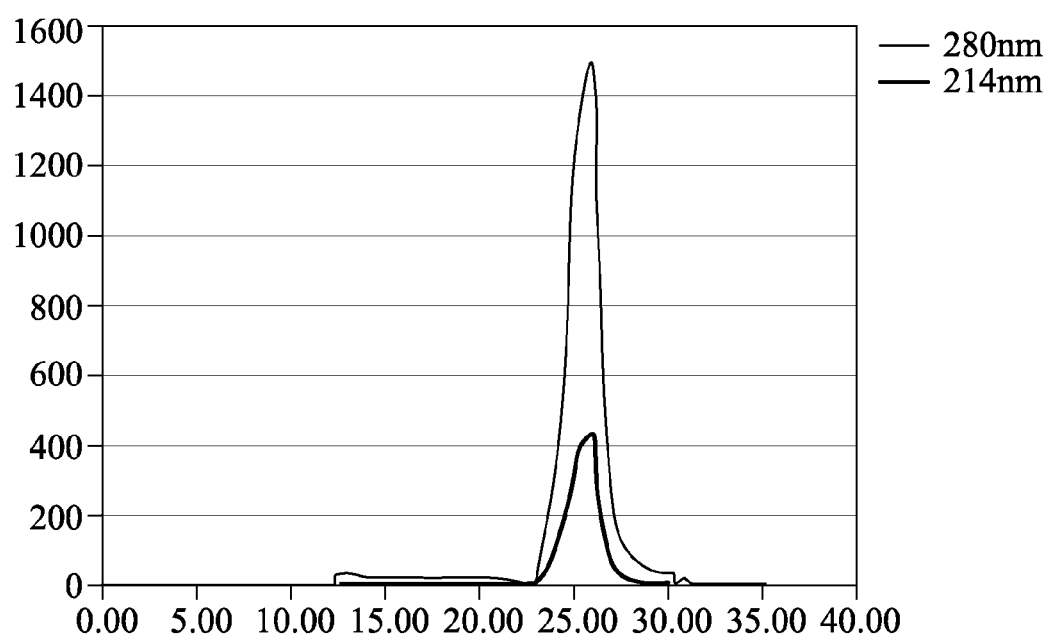

In this study, the high performance liquid chromatography was performed to analyze the studied metal complex, which was cleaved by MMP-2. As shown in FIG. 1(II), the metal complex ([Gd(NBCB-TTDA-(L)-MMP-2)]$^{2-}$) of the present invention produced three peaks after being cleaved by MMP-2. As shown in FIG. 2, the metal complex ([Gd(NBCB-TTDA-(D)-MMP-2)]$^{2-}$) of the Comparative Example produced only one peak after adding MMP-2. It has been proved that the metal complex of the present invention has specificity to matrix metalloprotease 2 (MMP-2), and is thus applicable to the preparation of MRI contrast agents for detecting atherosclerosis. The metal complex having the structural formula (V) of the present invention also has specificity to matrix metalloprotease 2 (MMP-2).

Study 3: In Vitro Image Study by a Magnetic Resonance Imaging Scanner

The metal complex ([Gd(NBCB-TTDA-(L)-MMP-2)]$^{2-}$) of the present invention was used for the in vitro image study. 0.2 mg (dissolved in 200 μl of PBS (0.5 mM)), 0.4 mg (dissolved in 200 μl of PBS (1 mM)) and 0.6 mg (dissolved in 200 μl of PBS (1.5 mM)) of the metal complex [Gd(NBCB-TTDA-(L)-MMP-2)]$^{2-}$ of the present invention were respectively added with MMP-2 (purchased from SIGMA), and the reaction was performed for 30 minutes, and then HSA (purchased from SIGMA) was added into the reaction to react for 30 minutes. Then, the metal complex [Gd(NBCB-TTDA-(L)-MMP-2)]$^{2-}$ without binding to HSA was separated by ultrafiltration (Microcon YM-30). The solution was scanned and analyzed by the 3.0 T magnetic resonance imaging scanner (Sigma; GE Medical Systems, Milwaukee, Wis.) using $T_1$ weighted imaging. The signal strength was shown in FIG. 3A and FIG. 3B.

Figure 3A:
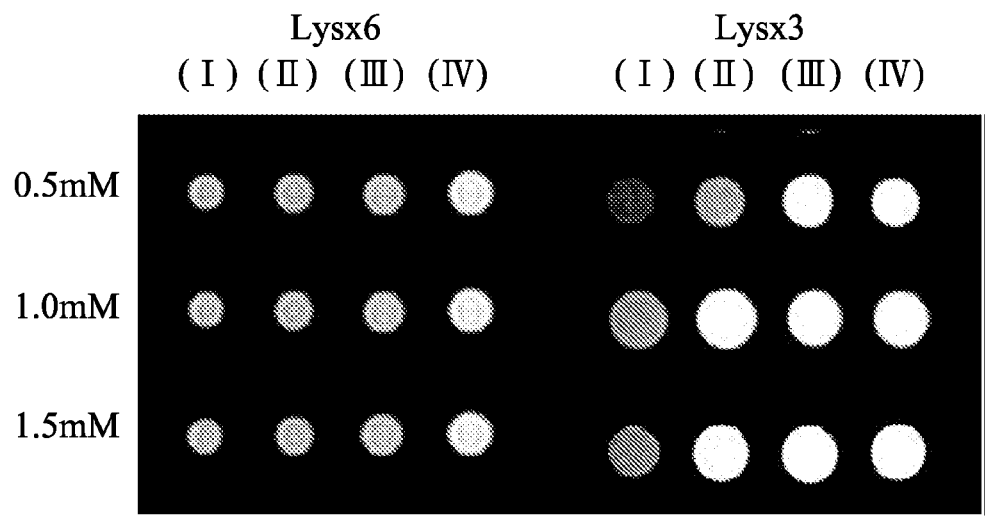
FIG. 3A shows the result of MR imaging by using the metal complex ([Gd(NBCB-TTDA-(L)-MMP-2)]$^{2-}$) of the present invention.
Figure 3B:
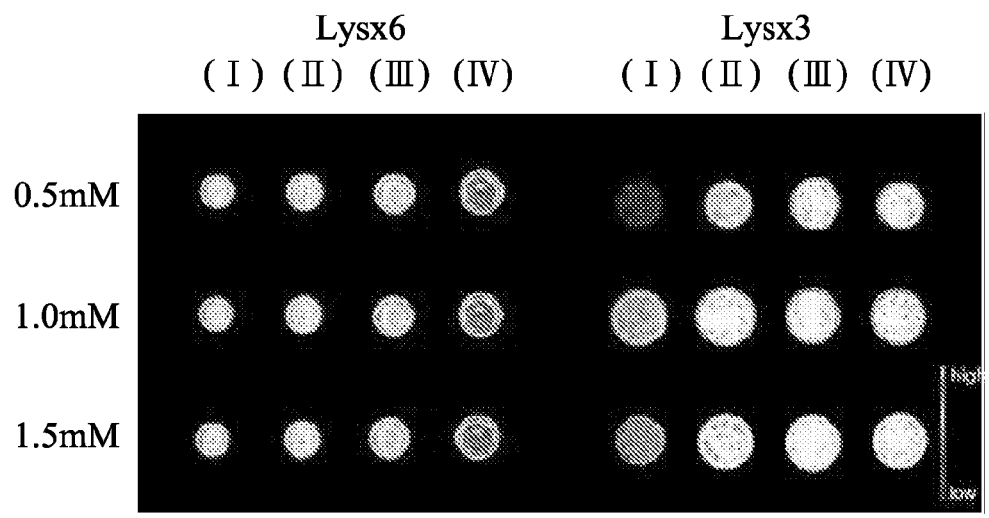
FIG. 3B shows the colorful image of FIG. 3A.

As shown in FIG. 3A and FIG. 3B, in comparison with the metal complex of the present invention including the MMP-2 sequence attached with 3 lysines, the metal complex of the present invention including the MMP-2 sequence attached with 6 lysines had more water solubility, had more hydrophobicity upon cleavage, and thus had increased binding to HSA, so as to have significantly improved image contrast.

Study 4: In Vivo Image Study by a Magnetic Resonance Imaging Scanner

1. In vivo image, study by using the metal complex ([Gd(NBCB-TTDA-(L)-MMP-2)]$^{2-}$) having the structural formula (VI) of the present invention Balb/c mice (6-8 week old, purchased from National Laboratory Animal Center) were used. Before magnetic resonance imaging scanning, the mice were anesthetized with sodium pentobarbital (40-50 mg/kg) via intraperitoneal injection, and scanned by the magnetic resonance imaging scanner (Sigma; GE Medical Systems, Milwaukee, Wis.) after being injected with the metal complex [Gd(NBCB-TTDA-(L)-MMP-2)]$^{2-}$ (0.1 mmol/kg) of the present invention (Conditions of scanning: 3.0 T MR scanner, $T_1$-weighted MR imaging).

2. In Vivo Image Study of the Metal Complex [Gd(NBCB-TTDA-(D)-MMP-2)]$^{2-}$ of the Comparative Example Balb/c mice (6-8 week old, purchased from National Laboratory Animal Center) were used. Before magnetic resonance imaging scanning, the mice were anesthetized with sodium pentobarbital (40-50 mg/kg) via intraperitoneal injection, and scanned by the magnetic resonance imaging scanner (Sigma; GE Medical Systems, Milwaukee, Wis.) after being injected with the metal complex [Gd(NBCB-TTDA-(D)-MMP-2)]$^{2-}$ (0.1 mmol/kg) of the present invention (Conditions of scanning: 3.0 T MR scanner, $T_1$-weighted MR imaging).

In this study, the ApoE-mice (these mice easily suffer cardiovascular diseases) were fed with high cholesterol food to cause vascular thrombosis. The mice fed with normal food were presented as a control group. The metal complex (0.1 mmol/kg) was injected via tail vein injection, and the scanning was performed by the 3.0 T magnetic resonance imaging scanner (Sigma; GE Medical Systems, Milwaukee, Wis.). The image results were shown in FIG. 4 to FIG. 7.

Figure 4:
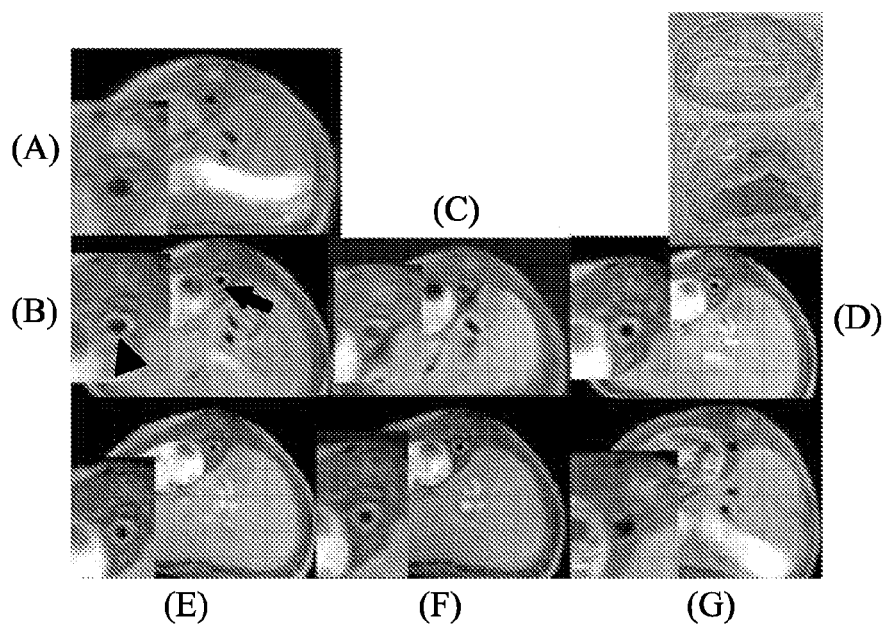
FIG. 4(A) to FIG. 4(G) show the image results of ApoE-mice having vascular thrombosis by injecting the metal complex ([Gd(NBCB-TTDA-(L)-MMP-2)]$^{2-}$) of the present invention, wherein (A) shows the image result before injecting the contrast agent, (B) shows the image result by injecting the contrast agent, (C) shows the image result by injecting the contrast agent for 10 minutes, (D) shows the image result by injecting the contrast agent for 20 minutes, (E) shows the image result by injecting the contrast agent for 30 minutes, (F) shows the image result by injecting the contrast agent for 120 minutes, and (G) shows the image result by injecting the contrast agent for 16 hours.
Figure 5:
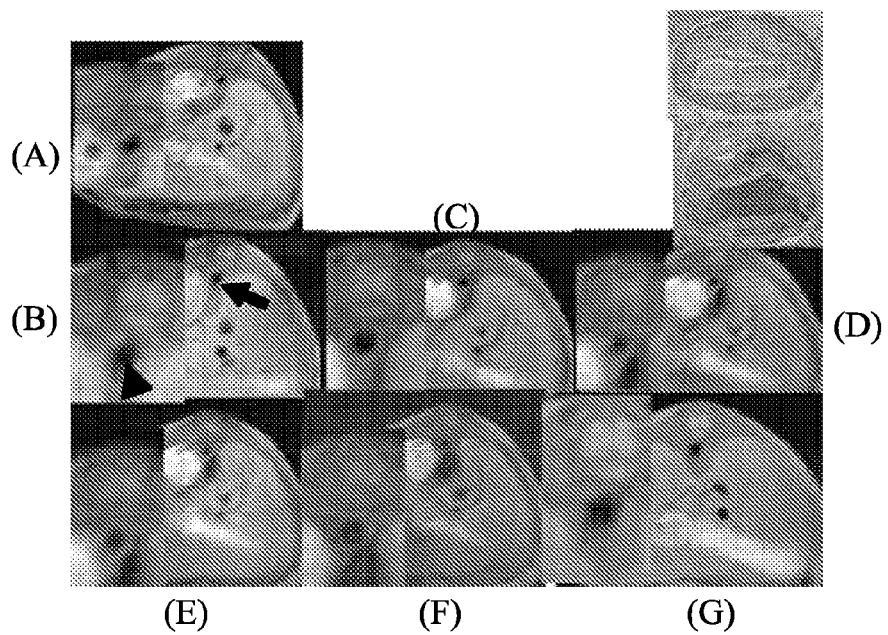
FIG. 5(A) to FIG. 5(G) show the image results of ApoE-mice having vascular thrombosis by injecting the metal complex ([Gd(NBCB-TTDA-(D)-MMP-2)]$^{2-}$) of the Comparative Example, wherein (A) shows the image result before injecting the contrast agent, (B) shows the image result by injecting the contrast agent, (C) shows the image result by injecting the contrast agent for 10 minutes, (D) shows the image result by injecting the contrast agent for 20 minutes, (E) shows the image result by injecting the contrast agent for 30 minutes, (F) shows the image result by injecting the contrast agent for 120 minutes, and (G) shows the image result by injecting the contrast agent for 16 hours.
Figure 6:
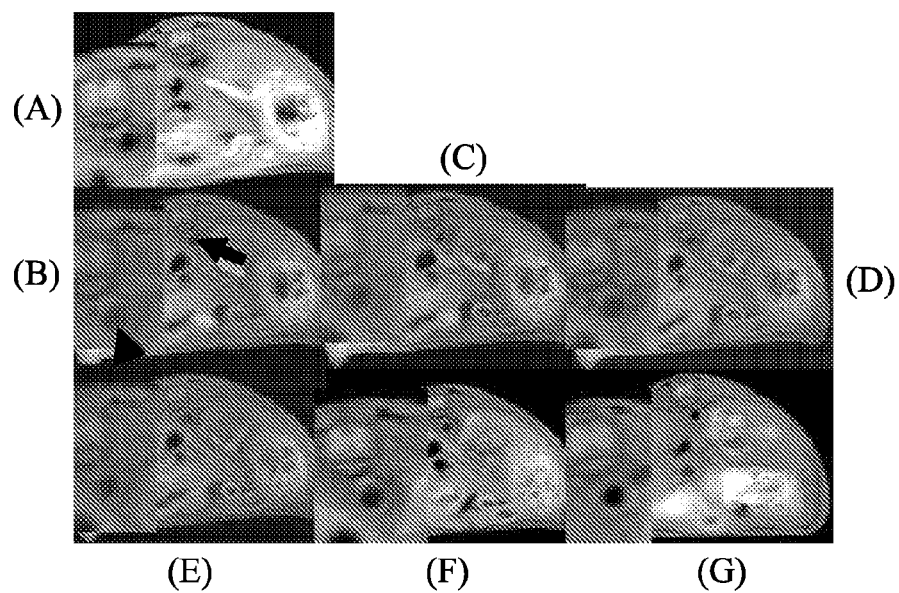
FIG. 6(A) to FIG. 6(G) show the image results of ApoE-mice without vascular thrombosis by injecting the metal complex ([Gd(NBCB-TTDA-(L)-MMP-2)]$^{2-}$) of the present invention, wherein (A) shows the image result before injecting the contrast agent, (B) shows the image result by injecting the contrast agent, (C) shows the image result by injecting the contrast agent for 10 minutes, (D) shows the image result by injecting the contrast agent for 20 minutes, (E) shows the image result by injecting the contrast agent for 30 minutes, (F) shows the image result by injecting the contrast agent for 120 minutes, and (G) shows the image result by injecting the contrast agent for 16 hours.

As shown in FIG. 4(B), the site with vascular thrombosis (indicated by a black arrow) significantly became brighter since the vascular plaque site secreted MMP-2, which cleaved the (L)-MMP-2 sequence in the metal complex [Gd(NBCB-TTDA-(L)-MMP-2)]$^{2-}$ of the present invention, so as to increase the hydrophobicity of the metal complex. Thus, the metal complex accumulated around the blood vessel, such that the image was brighter. In addition, as shown in FIG. 4, the metal complex of the present invention can be washed out from the mice in 16 hours.

As shown in FIG. 5(B), the mice with vascular thrombosis were injected with the metal complex [Gd(NBCB-TTDA-(D)-MMP-2)]$^{2-}$ of the Comparative Example, and the MMP-2 secreted from the vascular plaque would not cleave the (D)-MMP-2 sequence in the metal complex. Thus, the image had no improvement.

As shown in FIG. 6(B), the mice without vascular thrombosis were injected with the metal complex [Gd(NBCB-TTDA-(L)-MMP-2)]$^{2-}$ of the present invention, and since no MMP-2 was secreted, the (L)-MMP-2 sequence in the metal complex would not be cleaved. Thus, there was no change to the image.

Figure 7:
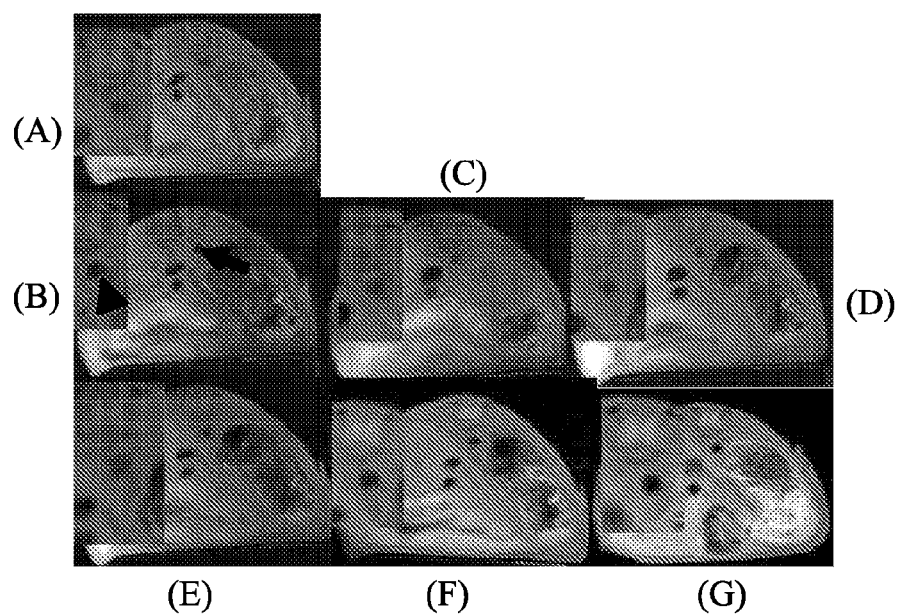
FIG. 7(A) to FIG. 7(G) show the image results of mice without vascular thrombosis by injecting the metal complex ([Gd(NBCB-TTDA-(D)-MMP-2)]$^{2-}$) of the Comparative Example, wherein (A) shows the image result before injecting the contrast agent, (B) shows the image result by injecting the contrast agent, (C) shows the image result by injecting the contrast agent for 10 minutes, (D) shows the image result by injecting the contrast agent for 20 minutes, (E) shows the image result by injecting the contrast agent for 30 minutes, (F) shows the image result by injecting the contrast agent for 120 minutes, and (G) shows the image result by injecting the contrast agent for 16 hours.

As shown in FIG. 7, the mice without vascular thrombosis were injected with the metal complex [Gd(NBCB-TTDA-(D)-MMP-2)]$^{2-}$ of the Comparative Example, and since no MMP-2 was secreted, the (D)-MMP-2 sequence in the metal complex would not be cleaved. Thus, there was no change to the image.

In accordance with the present invention, the metal complex includes the MMP-2 sequence, such that the hydrophobicity of the metal complex is increased while MMP-2 is secreted at the vascular plaque due to the vascular thrombosis to cleave the (L)-MMP-2 sequence of the metal complex, and thus the metal complex accumulates at the site with vascular thrombosis. Hence, the targeting contrast is achieved in the present invention.

Accordingly, the metal complex of the present invention has great relaxivity, has great binding to HSA, and has great effects in magnetic resonance imaging. It is clear that the metal complex of the present invention is applicable to the preparation of a contrast agent for detecting atherosclerosis.

The present invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

What is claimed is:

1. A ligand having a structural formula (I):

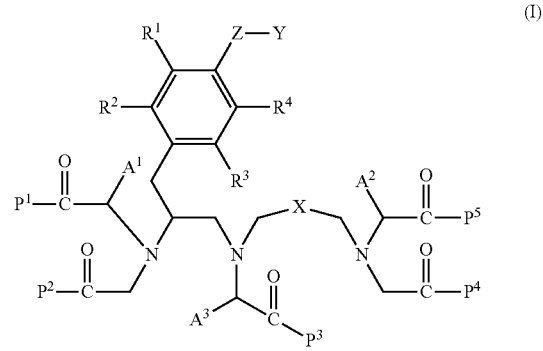

wherein
$R^1$, $R^2$, $R^3$ and $R^4$ are independently hydrogen, nitro, amino or thiocyano;
$P^1$, $P^2$, $P^3$, $P^4$ and $P^5$ are independently oxo, halo, hydroxyl or $C_{1-7}$alkyl;
X is methylenyl, 1,1-cyclobutylenyl, 1,1-cyclopentylenyl or 1,1-cyclohexanylenyl;
$A^1$, $A^2$ and $A^3$ are independently hydrogen, $C_{1-3}$ alkyl, $C_{1-3}$benzylalkyl, $C_{1-3}$methoxybenzylalkyl, diphenylmethyl or $C_{1-3}$isothiocyanobenzylalkyl;
Z is a group binding to Y; and Y has a structural formula (III):

$$\text{(III)}$$

wherein n is an integer in a range from 2 to 8.

2. The ligand of claim 1, wherein Z is $$-\overset{H}{N}-\overset{\overset{S}{\|}}{C}- \quad \text{or} \quad -\overset{H}{N}-\overset{\overset{O}{\|}}{C}-.$$

3. The ligand of claim 1, wherein the amino acid sequence comprises lysine and valine.

4. The ligand of claim 3, wherein the valine is L-valine.

5. The ligand of claim 1, wherein $P^1$, $P^2$, $P^3$, $P^4$ and $P^5$ are independently hydroxyl or oxo.

6. The ligand of claim 1, wherein $R^1$, $R^2$, $R^3$ and $R^4$ are independently hydrogen, X is 1,1-cyclobutylenyl, and $A^1$, $A^2$ and $A^3$ are independently hydrogen.

7. A metal complex, comprising:
   a paramagnetic metal ion; and
   a ligand chelating the paramagnetic metal ion and having a structural formula (I):

$$\text{(I)}$$

wherein
   $R^1$, $R^2$, $R^3$ and $R^4$ are independently hydrogen, nitro, amino or thiocyano;
   $P^1$, $P^2$, $P^3$, $P^4$ and $P^5$ are independently oxo, halo, hydroxyl or $C_{1-7}$alkyl;
   X is methylenyl, 1,1-cyclobutylenyl, 1,1-cyclopentylenyl or 1,1-cyclohexanylenyl;
   $A^1$, $A^2$ and $A^3$ are independently hydrogen, $C_{1-3}$ alkyl, $C_{1-3}$benzylalkyl, $C_{1-3}$methoxybenzylalkyl, diphenylmethyl or $C_{1-3}$isothiocyanobenzylalkyl;
   Z is a group bonding to Y; and Y has a structural formula (III):

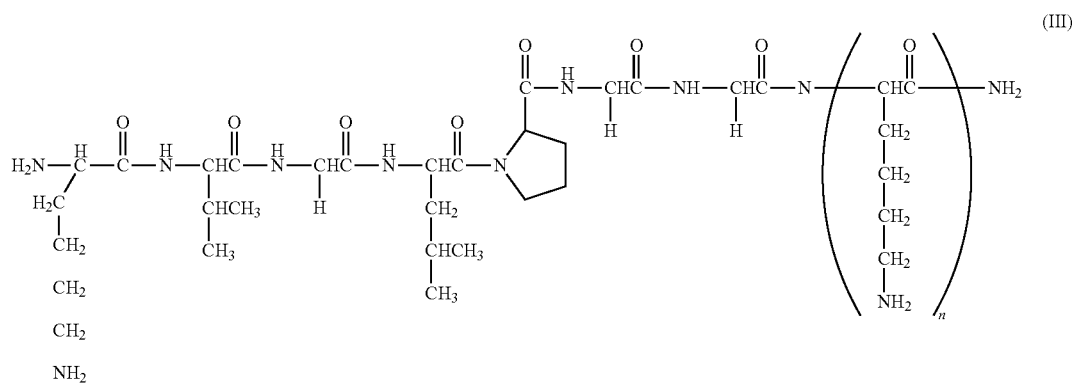

wherein n is an integer in a range from 2 to 8.

8. The metal complex of claim 7, wherein $P^1$, $P^2$, $P^3$, $P^4$ and $P^5$ are independently hydroxyl or oxo.

9. The metal complex of claim 7, wherein $R^1$, $R^2$, $R^3$ and $R^4$ are independently hydrogen, X is 1,1-cyclobutylenyl, and $A^1$, $A^2$ and $A^3$ are independently hydrogen.

10. The metal complex of claim 7, having a structural formula (II):

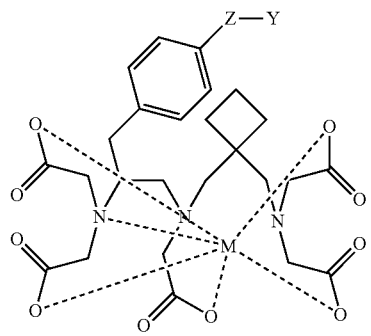

wherein

M is a metal ion selected from the group consisting of $Gd^{3+}$, $Mn^{2+}$ and $Fe^{3+}$, Z is

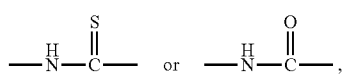

and

Y is an amino acid sequence comprising a matrix metalloprotease 2 sequence.

11. The metal complex of claim 10, wherein the amino acid sequence comprises lysine and valine.

12. The metal complex of claim 11, wherein the valine is L-valine.

13. The metal complex of claim 7, having a structural formula (VI):

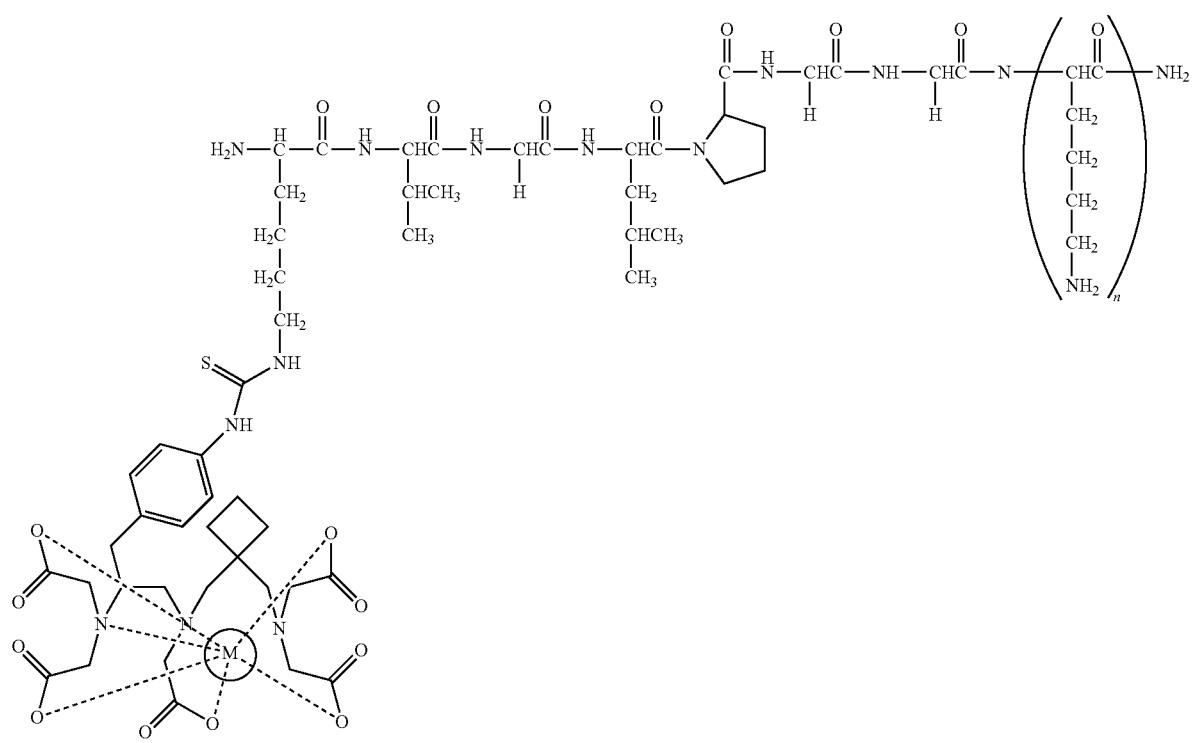
(IV)
wherein M is a metal ion selected from the group consisting of $Gd^{3+}$, $Mn^{2+}$ and $Fe^{3+}$, and n is an integer in a range from 2 to 8.
14. The metal complex of claim 13, wherein n is an integer in a range from 3 to 6.
15. The metal complex of claim 7, being used for preparing a magnetic resonance imaging contrast agent.
* * * * *